United States Patent [19]

Evans et al.

[11] Patent Number: 4,609,641

[45] Date of Patent: Sep. 2, 1986

[54] RENIN-INHIBITORY PEPTIDE ANALOGS

[75] Inventors: Ben E. Evans; Kenneth E. Rittle, both of Landsdale, Pa.

[73] Assignee: Merck & Co., Inc., Rahway, N.J.

[21] Appl. No.: 677,431

[22] Filed: Dec. 3, 1984

[51] Int. Cl.[4] .................. A61K 37/64; C07K 5/02; C07K 7/02

[52] U.S. Cl. .................... 514/16; 514/17; 514/18; 260/998.2

[58] Field of Search .................. 260/112.5 R; 514/18, 514/16, 17

[56] References Cited

U.S. PATENT DOCUMENTS 4,384,994 5/1983 Veber et al. ............... 260/112.5 R
4,397,786 8/1983 Evans et al. ............... 260/112.5 R

OTHER PUBLICATIONS

Boger et al., *Nature,* 303, 81–85 (1983).

Rudinger, *Peptide Hormones,* edited by Parsons, U. Park Press, Baltimore, 1–7 (1976).

*Primary Examiner*—Delbert R. Phillips
*Assistant Examiner*—F. T. Moezie
*Attorney, Agent, or Firm*—Richard A. Elder; Hesna J. Pfeiffer; Julian S. Levitt

[57] ABSTRACT

Peptides having the formula

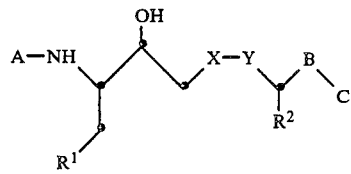

and their use as pharmaceuticals are disclosed.

4 Claims, No Drawings

RENIN-INHIBITORY PEPTIDE ANALOGS

BACKGROUND OF THE INVENTION

The invention is concerned with novel peptide analog renin inhibitors.

Peptide renin inhibitors are disclosed in the literature [See e.g. U.S. Pat. No. 4,384,994; European Patent Application No. 0,077,029; U.S. Pat. No. 4,397,786; Boger et al. *Nature* 303: 81–84 (1983)]. One class of such inhibitors contains the statine type amino acid residue of the formula

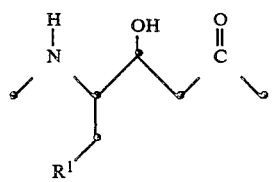

Peptide analog renin inhibitors have been discovered which contain a reduced statine residue of the formula

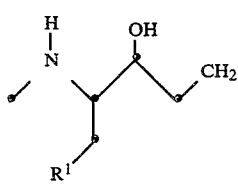

SUMMARY OF THE INVENTION

A peptide analog compound having the formula

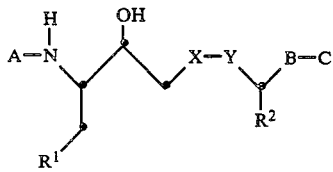

containing no statine amino acid residue.

DETAILED DESCRIPTION OF THE INVENTION

An embodiment of the present invention is a peptide analog compound of the formula:

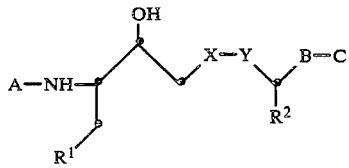

and pharmaceutically acceptable salts thereof wherein:
A is
(i)

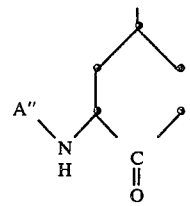

wherein:
A″ is hydrogen; or phenoxyacetyl;
(ii)

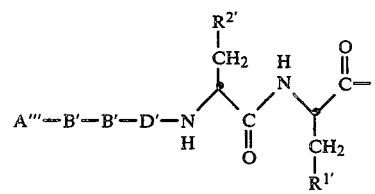

wherein:
A‴ is hydrogen;

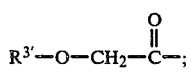
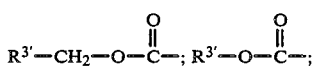
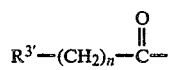

wherein n is 0–5; or

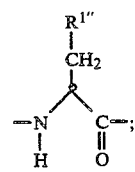

where $R^{3'}$ has the same meaning as set out further below, and may additionally be hydrogen;
B′ is absent; glycyl; or

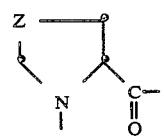

D′ is absent; or where Z is $(CH_2)_n$ and n is 1 or 2; or —S—;
$R^{1'}$ or $R^{1''}$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^{2'}$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl; and $R^{3'}$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo;

(iii)

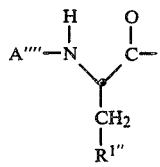 IV wherein:

A'''' is hydrogen; or

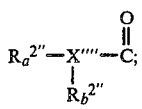

wherein:

X'''' is

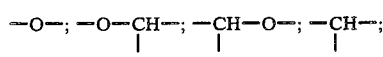

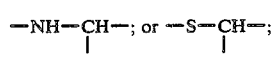

and $R_a{}^{2''}$ and $R_b{}^{2''}$ may be the same or different and are hydrogen; $Y'$—$(CH_2)_n$— or $Y'$—$(CH_2)_m$—CH=CH—$(CH_2)$—$_p$ where $Y'$ is hydrogen; aryl; aryl substituted with up to five members independently selected from the group consisting of $C_{1-8}$alkyl, trifluoromethyl, hydroxy, $C_{1-4}$alkoxy, and halo; n is 0 to 5; m is 0 to 2; and p is 0 to 2; except that where X'''' is —O—, only one of $R_a{}^{2''}$ or $R_b{}^{2''}$ is present; and $R^{1''}$ is hydrogen; $C_{1-4}$ alkyl, provided, that where $R^1$ is i-propyl, and B is Phe or Tyr, A is other than hydrogen or phenoxyacetyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy; fluoro, chloro, bromo, and iodo; indolyl; 4-imidazolyl; amine $C_{2-4}$alkyl; guanidyl $C_{2-3}$alkyl; or methylthiomethyl;

X-Y is

trans-CH=CH—

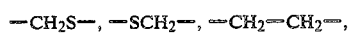

-continued

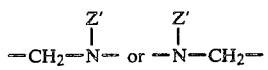

wherein

Z' is H, $CH_3$, $(CH_2)_nB''$, $(CH_2)_n$ C'' wherein n is 0-4, or

wherein $R_a$ is $C_1$–$C_6$ alkyl, ar-$C_{1-6}$-alkyl, $C_{3-7}$ cycloalkyl; $C_{1-6}$ alkoxy; aryl or heteroaryl;

$R^1$ is $C_1$–$C_4$ branched or linear alkyl $C_3$–$C_6$ cycloalkyl, phenyl or monosubstituted phenyl wherein the substituent is OH, Cl, F, Br, $CH_3$, $CF_3$, I or $OCH_3$, $R^2$ is hydrogen or

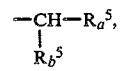

wherein $R_a{}^5$ and $R_b{}^5$ are independently selected from hydrogen, $C_1$–$C_4$ alkyl, hydroxy, phenyl or $C_3$–$C_7$ cycloalkyl;

B'' is

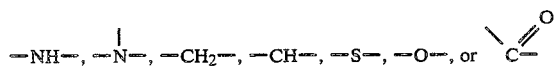

C'' is $NH_2$, $NHCH_2R^{3''}$, —NH— or

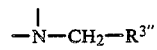

wherein $R^{3''}$ is $C_3$–$C_6$ alkyl, $C_3$–$C_7$ cycloalkyl, phenyl or mono-substituted phenyl wherein the substituent is methyl, trifluoromethyl, hydroxy, methoxy, fluoro, chloro, bromo or iodo; and B-C is

wherein $R^6$ is selected from:

(a)

B'''      V wherein

B''' is OR; NHR; or $NR_2$, where each R may be the same or different and is hydrogen or $C_{1-4}$ alkyl;

(b)

B''''—E      VI wherein

B'''' is absent; glycyl; or

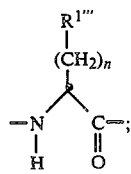

wherein
n is 1 or 2; or —S—;

R$^{1'''}$ is hydrogen; C$_{1-4}$ alkyl; hydroxy C$_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine C$_{2-4}$ alkyl; guanidyl C$_{2-3}$ alkyl; or methylthiomethyl; and E is OR; NHR, or N(R)$_2$, where each R may be the same or different and is hydrogen or C$_{1-4}$ alkyl; and (c)

$$B^\circ\text{—}D\text{—}E \qquad\qquad VII$$

wherein
B° is —Y—(CH$_2$)$_n$—R$^{6a}$ (1)
where
Y is —NH— or —O—;
n is 0 to 5; and R$^{6a}$ is hydrogen; hydroxy; C$_{1-4}$alkyl; C$_{3-7}$cycloalkyl; aryl; aryl substituted with up to five members independently selected from the group consisting of C$_{1-6}$alkyl, trifluoromethyl, hydroxy, C$_{1-4}$alkoxy, amino, mono- or di-C$_{1-4}$ alkylamino, and halo; amino; mono-, di-, or tri-C$_{1-4}$alkylamino; guanidyl; heterocyclic; or heterocyclic substituted with up to five members independently selected from the group consisting of C$_{1-6}$alkyl, hydroxy, trifluoromethyl, C$_{1-4}$alkoxy, halo, aryl, aryl C$_{1-4}$alkyl, amino, and mono- or di-C$_{1-4}$alkylamino;

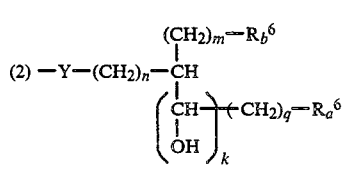

where
Y is as defined above;
n is 0 or 1;
k is 0 or 1;
q is 1 to 4;
m is 1 to 4; and R$_b^6$ and R$_a^6$ may be the same or different and have the same meaning as R$_a^6$ above and R$_a^6$ may additionally be

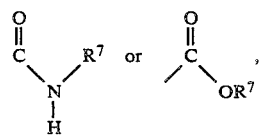

where R$^7$ is hydrogen or C$_{1-3}$alkyl;

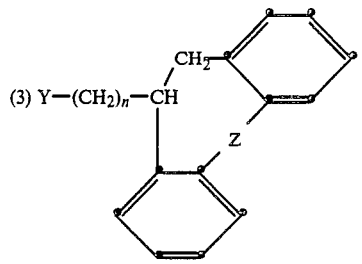

where
Y is as defined above;
n is 0 or 1; and
Z is

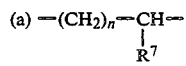

where
n is 0 or 1; and
R$^7$ is as defined above; or

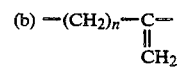

where
n is 0 or 1; or

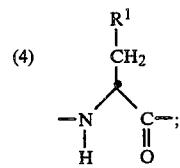

D is absent; glycyl; sarcosyl; or

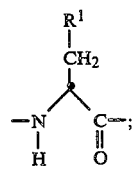

and

E is absent; OR; NHR; or N(R)$_2$; where R may be the same or different and is hydrogen or C$_{1-4}$alkyl; or (d)

$$\text{—E—} \qquad\qquad VIII$$

wherein:
E is —Y—(CH$_2$)$_n$—R$_a^6$ (1)
where
Y is —NH— or —O—;
n is 0 to 5; and
R$_a^6$ is hydrogen;
C$_{1-3}$alkyl;
C$_{3-7}$cycloalkyl; naphthyl; phenyl; phenyl substituted with up to five members independently selected from the group consisting of methyl, trifluoromethyl, hydroxyl, methoxy, amino, fluoro, chloro, bromo, and iodo; imidazolyl; pyridyl; pyrryl; hydroxyl; amino; $C_{1-4}$alkyl mono-, di-, or tri-substituted amino; guanidyl; piperidyl; tetrahydropyrryl; or N-substituted piperidyl or tetrahydropyrryl where the N-substituent is a member selected from the group consisting of hydrogen, $C_{1-6}$alkyl, $C_{1-6}$hydroxyalkyl, phenyl, benzyl, naphthyl, and naphthylmethyl;

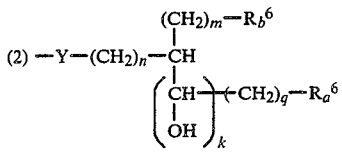

where
Y is as defined above;
n is 0 or 1;
k is 0 or 1;
q is 1 to 4;
m is 1 to 4; and
$R_b^6$ and $R_a^6$ may be the same or different and have the same meaning as $R_a^6$ above; or

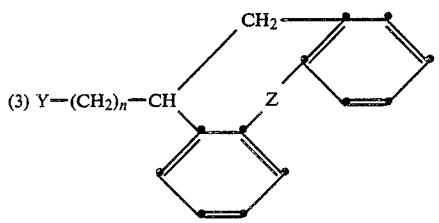

where
Y is as defined above;
n is 0 or 1; and
Z is

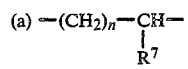

where
n is 0 or 1; and
$R^7$ is hydrogen or $C_{1-3}$alkyl; or

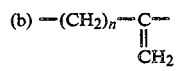

where
n is 0 or 1;
and pharmaceutically acceptable salts thereof.

The pharmaceutically acceptable salts of Formula I compounds include those derived from inorganic or organic acids as well as quaternary salts. Included among such acid derived salts are the following: acetate, adipate, alginate, aspartate, benzoate, benzenesulfonate, bisulfate, butyrate, citrate, camphorate, camphorsulfonate cyclopentanepropionaten, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, isethionate, lactate, maleate, methanesulfonate, 2-naphthalenesulfonate, nicotinate, oxalate, pamoate, phosphate, pectinate, persulfate, 3-phenylpropionate, picrate, pivalate, propionate, succinate, tartrate, thiocyanate, tosylate, undecanoate. Also, the basic nitrogen-containing groups can be quaternized with such agents as lower alkyl halide, such as methyl, ethyl, propyl, and butyl chloride, bromides and iodides; and diamyl sulfates, long chain halides such as decyl, lauryl, myristyl and stearyl chlorides, bromides and iodides, aralkyl halides like benzyl and phenethyl bromides and others.

The peptides of Formula I are characterized by containing a reduced statine unit of the formula:

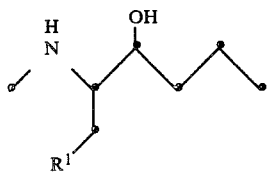

Preferred definitions of $R^1$ are $C_1-C_6$ alkyl and cycloalkyl, especially —CH(CH$_3$)$_2$, phenyl, and cyclohexyl.

The N-terminal group $A^1$ comprises three units designated as (i), (ii) and (iii).

The (i) unit is represented by formula II and is defined above. The preferred (i) units are: N-phenoxyacetyl-L-leucyl and L-leucyl-.

The (ii) unit is represented by formula III and is defined above. In the definition of formula III, alkyl is intended to include branched and linear moieties. Common acid components of formula III are exemplified by:
B' is absent, Gly, Ala, Val, Leu, Ile, Phe, Tyr, Trp, His, Lys, Orn, Arg, or Met;
D' is absent or Pro.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the definition of common amino acids.

The preferred (ii) units are:
His-Pro-Phe-His;
Isovaleryl-His-Pro-Phe-His;
Acetyl-Pro-Phe-His;
Acetyl-Phe-His;
tert-Butyloxycarbonyl-Phe-His;
tert-Butyloxycarbonyl-His-Pro-Phe-Phe;
Isobutyryl-His-Pro-Phe-His;
Isobutyryl-His-Pro-Phe-His;
tert-Butyloxycarbonyl-His-Pro-Phe-His;
tert-Butyloxycarbonyl-His-Pro-Phe-His;
Isobutyryl-His-Pro-Phe-His; and
tert-Butyloxycarbonyl-Phe-Phe.

The (ii) unit is represented by the formula IV and is defined above. In the definition of formula IV, alkyl includes both straight and branched chain moieties—halo includes F, Cl, Br and I—aryl represents phenyl and naphthyl—the heterocyclic substituent represents any 5- or 6-membered aromatic ring containing from one to three heteroatoms selected from the group consisting of nitrogen, oxygen, and sulfur; having various degrees of saturation; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl isothiazolyl, isothiazolidinyl, indolyl, quinolinyl, isoquinolinyl, benzimidazolyl, benzothiazolyl, benzoxazolyl, furyl, thienyl and benzothienyl.

Where the heterocyclic substituent itself is substituted, it is preferred that the substituent be aryl $C_{1-4}$ alkyl.

Preferred (iii) units are:
His-;
BOC-His-;
POA-His-;
3-phenylpropionyl-His-;
2-methyl-3-phenylpropionyl-His-;
2-ethyl-3-phenylpropionyl-His-;
2,3-diphenylpropionyl-His-;
2-benzyl-3-phenylpropionyl-His-;
2-phenethyl-3-phenylpropionyl-His-;
2-phenylpropyl-3-phenylpropionyl-His-;
2-phenylbutyl-3-phenylpropionyl-His-;
2-phenethenyl-3-phenylpropionyl-His-;
2-(4,4-dimethyl-1-butenyl)-3-phenylpropionyl-His-;
10,11-dihydro-5H-dibenzo[2,d]cycloheptenylcarbonyl-His-; and
BOC-His-.

Especially preferred (iii) units are: POA-His- and 2-phenylpropyl-3-phenylpropionyl-His-.

The C-terminal group B'-C' is represented by the formula:

where $R^6$ is one of four units designated (a), (b), (c) and (d).

The (a) unit is represented by formula V and is defined above. A preferred (a) unit is phenylalanine. The (b) unit is represented by formula VI and is defined above. Common amino acids which are included in the definition of B''' in formula VI are Gly, Ala, Val, Leu, Ile, Phe, Tyr, Trp, His, Lys, Orn, Arg and Met. The term common amino acids is also meant to include closely related analogs e.g. aliphatic amino acids such α-aminobutyric acid (Abu) substituted phenyl derivatives of Phe and the like. Preferred (b) units are Phe—NH$_2$, Leu OCH$_3$, Tyr—NH$_2$ and Lys—NH$_2$.

The (c) unit is represented by formula VII and is defined above. Preferred (c) units are:
Leu-Phe-methyl ester;
Phe-Phe-methyl ester;
Ala-Phe-methyl ester;
Leu-Phe-amide;
Phe-Phe-amide;
Leu-benzylamide;
Ile-benzylamide; and
Ile-2-pyridylmethylamide.

More preferred (c) units are:
Leu-Phe-amide;
Leu-benzylamide;
Ile-benzylamide; and
Ile-2-pyridylmethylamide.

The (d) unit is represented by the formula VIII and is defined above. Preferred (d) units are:
Leu-benzylamide;
Leu-2-phenylethylamide;
Leu-3-phenylpropylamide;
Leu-1,2-diphenylethylamide;
Leu-(+)-1,2-diphenylethylamide;
Leu-(−)-1,2-diphenylethylamide;
Leu-(+)-α-phenylethylamide;
Leu-(−)-α-phenylethylamide;
Leu-(+)-α-naphthylethylamide;
Leu-(−)-α-naphthylethylamide;
Leu-p-chlorobenylamide;
Leu-p-methoxybenzylamide;
Leu-10,11-dihydro-5H-dibenzo[a,d]cycloheptenea-mide; and
Leu-D,L-threo-1,2-diphenyl-2-hydroxyethylamide.

Preferred X—Y are

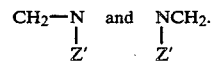

More preferred are

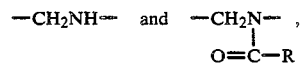

especially

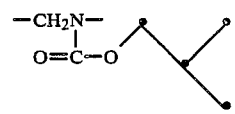

The (+) and (−) designations in these preferred units refers to the optical rotation of the amine.

It is preferred that in the formula I peptide analogs the asymmetric carbon atoms are in the S configuration, except for the E moiety in which the carbon atom may be in the S or R configuration.

Each of the possible combinations of the N-terminal units (i) through (iii) with the C-terminal units (a) through (d) constituted a preferred embodiment of the present invention.

A more preferred embodiment is the peptide analog of formula I where the N-terminal unit is Boc-Phe-Phe and the C-terminal unit is Leu-benzylamide. A most preferred embodiment is the peptide analog of formula I where the N-terminal unit is Boc-Phe-His and the C-terminal unit is Leu-benzylamide. Another embodiment of the present invention is a pharmaceutical composition containing a renin-inhibitory amount of a compound of formula I or pharmaceutically acceptable salt thereof. The composition, may, if required, be formulated using convention carriers diluents, excipients and the like.

The formula I peptide analogs possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The peptides analogs of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Another embodiment of the present invention is a method of treating renin-associated hypertension and hyperaldosteronism, omprising administering to a patient in need of such reatment a therapeutically effective amount of a peptide analog of formula I or a pharmaceutically acceptable salt thereof.

The renin inhibitory peptide analogs of the present invention may also be utilized in diagnostic methods for the purpose of establishing the significance of renin as a causative or contributory factor in hypertension or hyperaldosteronism in a particular patient. For this purpose the peptide analogs of the present invention may be administered in a single dose of from 0.1 to 10 mg per kg of body weight.

Both in vivo and in vitro methods may be employed. In the in vivo method, a novel peptide analog of the present invention is administered to a patient, preferably by intravenous injection, although parenteral administration is also suitable, at a hypotensive dosage level and as a single dose, and there may result a transitory fall in blood pressure. This fall is blood pressure, if it occurs, indicates supranormal plasma renin levels.

An in vitro method which may be employed involves incubating a body fluid, preferably plasma, with a novel peptide analog of the present invention, and after deproteinization, measuring the amount of angiotensin II produced in nephrectomized, pentolinium-treated rats. Another in vitro method involves mixing the plasma or other body fluid with a novel peptide analog of the present invention and injecting the mixture into a test animal. The difference in pressor response with and without added peptide analog is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptide analogs of the present invention may be prepared in accordance with well-known procedures for preparing peptides from their constituent amino acids, which will be described in more detail below. The unusual amino acid, statine, may be prepared in accordance with the procedure described in Rich et al., *J. Org. Chem.* 43: 3624 (1978).

The peptide analogs of the present invention may be prepared by using a conventional solution or solid phase sequential synthesis technique.

Abbreviated designations are used herein for amino acids components, certain preferred protecting groups, reagents, solvents, etc. The meanings of such abbreviated designations are given below.

| Abbreviated Designation | |
|---|---|
| | Amino Acid |
| Ala | L-alanine |
| Arg | L-arginine |
| Gly | L-glycine |
| His | L-histidine |
| Ile | L-isoleucine |
| Leu | L-leucine |
| Lys | L-lysine |
| Met | L-methionine |
| Orn | L-ornithine |
| Phe | L-phenylalanine |
| Pro | L-proline |
| Ser | L-serine |
| Sta | (3S,4S)—statine |
| Thr | L-threonine |
| Trp | L-tryptophan |
| Tyr | L-tyrosine |
| Val | L-valine |
| | Protecting Groups |
| BOC | tert-butyloxycarbonyl |
| CBZ | benzyloxycarbonyl |
| DNP | dinitrophenyl |
| OMe | methyl ester |
| | Activating Groups |
| HBT | 1-hydroxybenzotriazole |
| ONp | p-nitrophenyl |
| | Condensing Agents |
| DCCI | dicyclohexylcarbodiimide |
| DPPA | diphenylphosphorylazide |
| EDC | 1-ethyl-3-(3-dimethylaminopropyl)-carbodiimide hydrochloride |
| | Reagents |
| TEA | triethylamine |

| Abbreviated Designation | |
|---|---|
| TFA | trifluoroacetic acid |
| POA | phenoxyacetyl |
| IBU | isobutyryl |
| | Solvents |
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptide analogs of the present invention is conducted in a stepwise manner either in solution in a solvent such as dichloromethane or DMF, or by the solid phase technique on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethylmethyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONp ester, an amino acid azide, and the like. Deprotection and addition of successive amino acids is performed until the desired linear peptide is formed. The separately synthesized dipeptide analog represented by formula I wherein A' is H and B'—C' is COOH is treated in this sequence as a conventional amino acid, except that protection of the X and/or Y moiety may be advantageous.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the ε-amino group of Lys can be protected by the INOC group or the 2-chlorobenzyloxycarbonyl (2-Cl-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptide analogs of the present invention is illustrated in the following examples, summarized in Schemes 1 and 2.

SCHEME 1

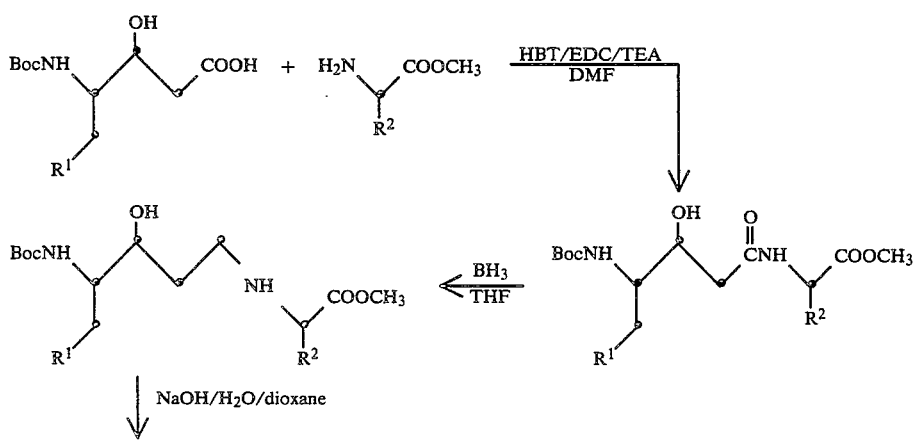

-continued
SCHEME 1
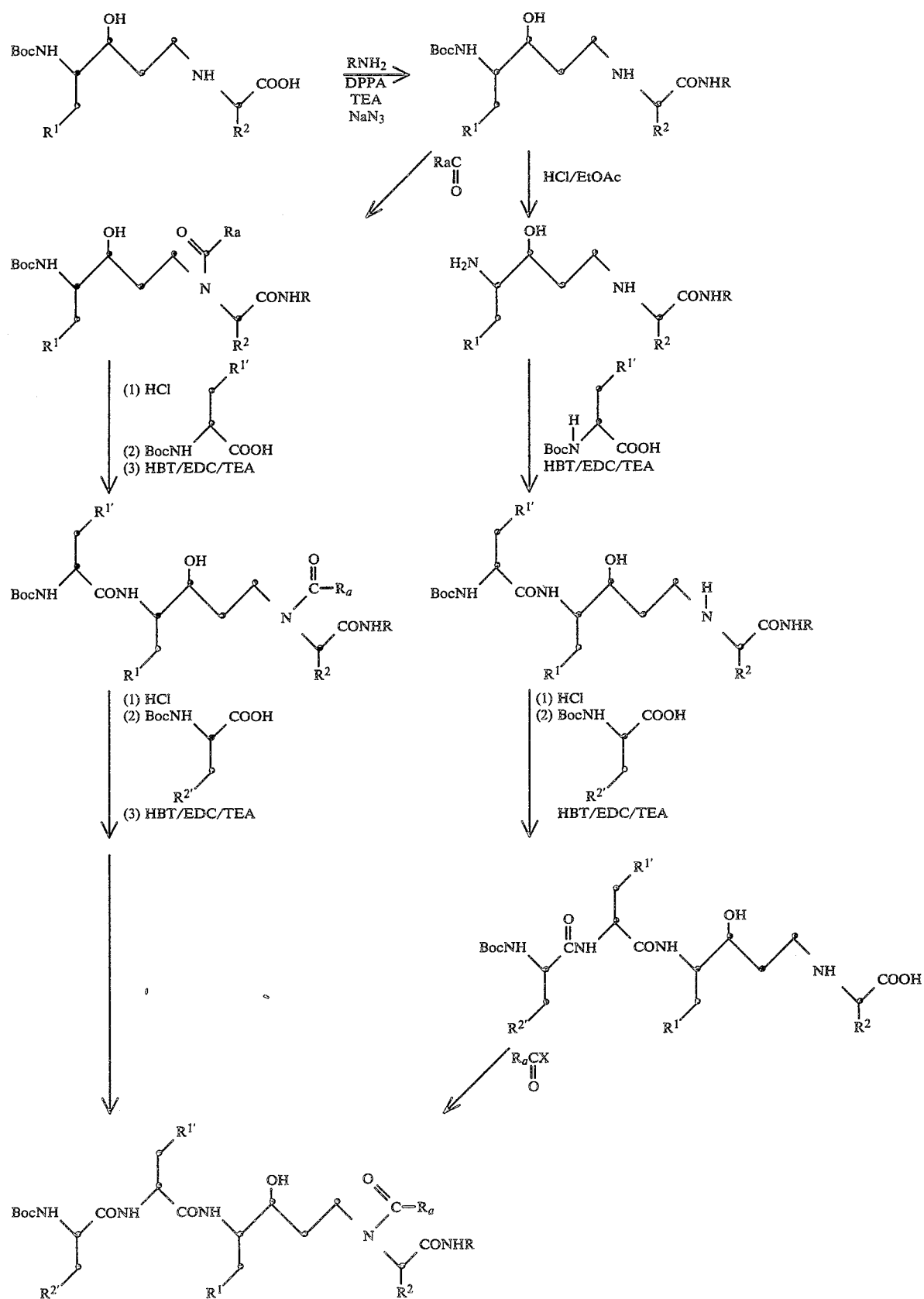

SCHEME 2
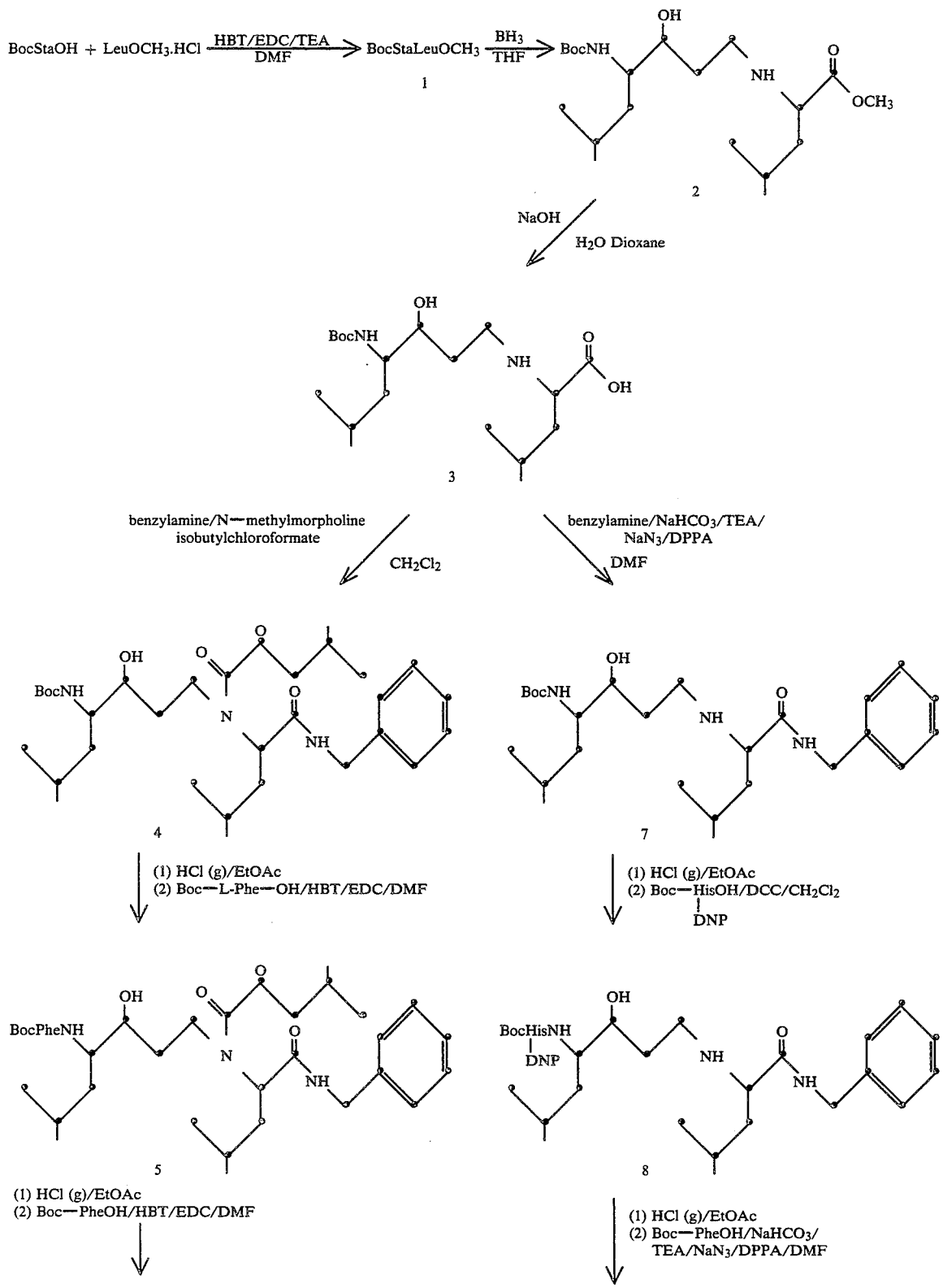

-continued
SCHEME 2

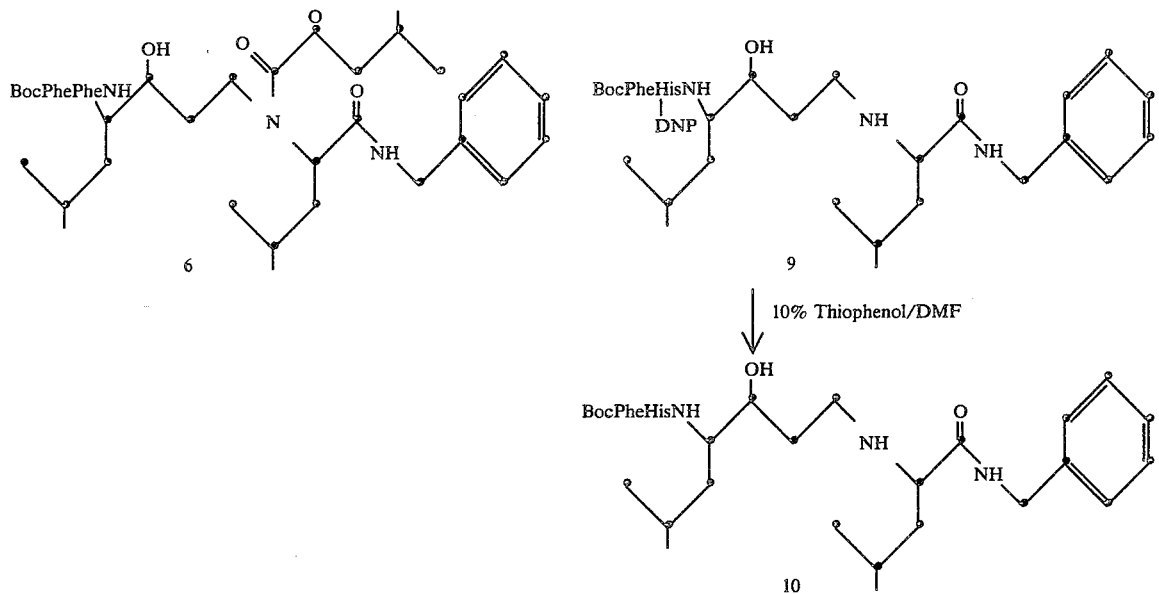

EXAMPLE 1

N$^\alpha$-tert-Butoxycarbonyl-(3S,4S)-statyl-L-leucine methyl ester 1

Boc-(3S,4S)-statine (1.25 g), leucine methyl ester hydrochloride (0.99 g), HBT (0.74 g), and EDC (1.05 g) were dissolved in DMF (20 ml) under a nitrogen atmosphere. The pH of the solution was adjusted to 9.0–9.5 with TEA (2 ml) and the reaction stirred 1 hour at 25° C. After removal of the DMF in vacuo, the residue was treated with 10% citric acid and extracted with EtOAc (3x). The combined extracts were washed with 10% citric acid (1x), H$_2$O (1x), saturated NaHCO$_3$ (aqueous) (2x), and brine (1x), dried over MgSO$_4$, filtered and evaporated to dryness in vacuo to give a crude light yellow oil (2.10 g). Flash chromatography on silica gel (35% EtOAc/hexane) gave 1 as a colorless oil (1.7 g, 95% yield).

TLC: silica GF (2% MeOH in CH$_2$Cl$_2$), R$_f$32 0.31, single homogeneous component.
PMR: consistent with structure.
HPLC: 90.0%.
MS (FAB): m.w.=403 m/e (M+H).
SPINCO: calc'd: Leu, 2.48. Found: Leu, 2.51.

N$^\alpha$-[4(S)-tert-Butoxycarbonylamino-3(S)-hydroxy-6-methylheptyl]-L-leucine methyl ester 2

1 (1.7 g) was dissolved in THF (9.0 ml), cooled to −25° C., and treated with 1M BH$_3$ in THF (9.2 ml. After stirring at −25° C. for 1 hour, the reaction was placed in the freezer at −10° C. for 16 hours. Upon removal from the freezer, the reaction was treated with MeOH (20 ml) and stirred 3 hours at room temperature. The MeOH was removed in vacuo and the residue treated with MeOH and restripped 2x. The crude residue was flash chromatographed on silica gel (30% EtOAc/hexane) to give a mixture of the desired product 2 and the amine-borane complex of 2 as a crude oil. The oil was dissolved in MeOH (15 ml), stirred 24 hours, and repeatedly evaporated with MeOH (3x) to give 2 (1.0 g, 61% yield).

TLC: silica GF (3% MeOH in CH$_2$Cl$_2$), R$_f$=0.36, essentially clean component.
PMR: consistent with structure.
MS (FAB): m.w.=389 m/e (M+H).

N$^\alpha$-[4(S)-tert-Butoxycarbonylamino-3(S)-hydroxy-6-methylheptyl]-L-leucine 3

2 (700 mg) was dissolved in dioxane (8 ml), diluted with H$_2$O (8 ml) and treated with four portions (2 ml each) of 1N NaOH (aqueous) over a 1.5 hour period. The aqueous dioxane was removed in vacuo and the white solid residue dissolved in H$_2$O (10 ml). The product was precipitated by acidification with 1N HCl and collected by filtration to give 3 as a fine white powder (560 mg, 83% yield) after drying.

TLC: silica GF (10/5/1/3 of EtOAc/pyridine/AcOH/H$_2$O), R$_f$=0.81, single homogeneous component.
PMR: consistent with structure.

N$^\alpha$-[4(S)-(tert-Butoxycarbonylamino)-3(S)-hydroxy-6-methylheptyl]-N$^\alpha$-isobutoxycarbonyl-L-leucine benzylamide 4

3 (560 mg) and N-methylmorpholine (0.165 ml) were combined in CH$_2$Cl$_2$ (6 ml) and cooled to −5° C. The suspension was treated with isobutylchloroformate (0.195 ml), stirred 15 minutes, treated with benzylamine (0.196 ml), and stirred 1 hour. After removal of CH$_2$Cl$_2$ in vacuo, the residue was treated with 10% citric acid and extracted with n-butanol (3x). The combined extracts were washed with 10% citric acid (1x), H$_2$O (2x), 10% NaHCO$_3$ (aqueous) (2x) and H$_2$O (1x), dried over MgSO$_4$, filtered and stripped to dryness in vacuo to give a white sticky solid (740 mg). Flash chromatography on silica gel (90/10/1/1 of CH$_2$Cl$_2$/MeOH/H$_2$O/HOAc) gave recovered 3 (260 mg) as well as the desired 4 (480 mg).

TLC: silica GF (5% MeOH in CH$_2$Cl$_2$), R$_f$=0.57, single homogeneous component.

PMR: consistent with structure.
MS (FAB): m.w.=564 m/e (M+H).

N$^\alpha$-[4(S)-(tert-Butoxycarbonyl-L-phenylalanylamino)-3(S)-hydroxy-6-methylheptyl]-N$^\alpha$-isobutoxycarbonyl-L-leucinebenzylamide 5

4 (320 mg) was dissolved in EtOAc (10 ml), cooled to 0° C., saturated with HCl (g), and stirred for 15 minutes. The solvent was removed in vacuo. The residue was treated with EtOAc and restripped (3x) to give a foam (290 mg). TLC (as free base): silica GF (5% MeOH in CH$_2$Cl$_2$), R$_f$=0.23, single homogeneous component. The foam (290 mg) was combined with Boc-L-Phe-OH (185 mg), HB (94.1 mg), and EDC (134 mg) in DMF (4 ml) under a trogen atmosphere. The pH of the solution was adjusted to 9.5 with TEA (0.300 ml) and the reaction stirred 2.5 hours at 25° C. After removal of the DMF in vacuo, the residue was treated with 10% NaHCO$_3$ (aqueous) and extracted with EtOAc (3x). The combined extracts were washed with 10% NaHCO$_3$ (aqueous) (1x) and brine (1x), dried over MgSO$_4$, filtered, and stripped to dryness in vacuo to give a yellow oil (360 mg). Flash chromatography on silica gel (30% EtOAc in hexane) gave 5 as a colorless oil (200 mg).
TLC: silica GF (3% MeOH in CH$_2$Cl$_2$), R$_f$=0.41, single homogeneous component.
PMR: consistent with structure.
MS (FAB): m.w.=711 m/e (M+H).
SPINCO: calc'd: Phe, 1.41. Found: Phe, 1.25.

N$^\alpha$-[4(S)-(tert-Butoxycarbonyl-L-phenylalanyl-L-phenylalanylamino)-3(S)-hydroxy-6-methylheptyl]-N$^\alpha$-isobutoxycarbonyl-L-leucine benzylamide 6

5 (200 mg) was dissolved in EtOAc (5 ml), cooled to 0° C., saturated with HCl (g), and stirred for 15 minutes. The solvent was removed in vacuo. The residue was treated with EtOAc and restripped (3x) to give a foam (200 mg). TLC (as free base): silica GF (3% MeOH in CH$_2$Cl$_2$), R$_f$=0.34, clean homogeneous component. The foam (190 mg) was combined with Boc-L-Phe (86.5 mg), HBT (44.0 mg), and EDC (62.6 mg) in DMF (4 ml) under a nitrogen atmosphere. The pH of the solution was adjusted to 9.5 with TEA (0.230 ml) and the reaction stirred 5 hours at 25° C. After removal of the DMF in vacuo, the residue was treated with 10% NaHCO$_3$ (aqueous) and extracted with EtOAc (3x). The combined extracts were washed with 10% NaHCO$_3$ (aqueous) (1x) and brine (1x), dried over MgSO$_4$, filtered, and stripped to dryness in vacuo to give a crude oil (260 mg). After flash chromatography on silica gel (450/10/1/1 of CH$_2$Cl$_2$/MeOH/H$_2$O/HOAc) the product was further purified by HPLC on a Chromega C-18 column (CH$_3$CN with 0.1% TFA in H$_2$O as buffer) to give 6 as a white foam (55 mg) from EtOAc.
TLC: silica GF (3% MeOH in CH$_2$Cl$_2$), R$_f$=0.46, single homogeneous component.
PMR: consistent with structure.
HPLC: 98%.
MS (FAB): m.w.=858 m/e (M+H).
SPINCO: calc'd: Phe, 2.33. FOUND: Phe, 2.31.

EXAMPLE 2

N$^\alpha$-[4(S)-tert-Butoxycarbonylamino-3(S)-hydroxy-6-methylheptyl]-L-leucine benzylamide 7

3 (540 mg) was suspended in DMF (23 ml) and treated with benzylamine (0.374 ml), TEA (0.401 ml), NaHCO$_3$ (solid) (924 mg) and sodium azide (117 mg). The suspension was cooled to −30° C., treated with DPPA (0.934 ml), and stirred at 0° C. for 72 hours. After removal of the DMF in vacuo, the residue was treated with 10% citric acid and extracted with EtOAc (3x). The combined extracts were washed with 10% citric acid (1x), H$_2$O (1x), 10% NaHCO$_3$ (aqueous) (1x), and brine (1x), dried over MgSO$_4$, filtered and evaporated to dryness in vacuo to give a crude colorless oil (1.5 g). Flash chromatography on silica gel (90/10/1/1 of CH$_2$Cl$_2$/MeOH/H$_2$O/HOAc) gave 7 as a sticky foam (440 mg).
TLC: silica GF (80/10/1 of CH$_2$Cl$_2$/MeOH/concentrated NH$_4$OH), R$_f$=0.72, single homogeneous component.
PMR: consistent with structure.
HPLC: 98.7%.
MS (FAB): m.w.=464 m/e (M+H).

N$^\alpha$-[4(S)-N$^\alpha$-(tert-Butoxycarbonyl-N'-2,4-dinitrophenyl-L-histidylamino)-3(S)-hydroxy-6-methyl-1-heptyl]-L-leucine benzylamide 8

7 (425 mg) was dissolved in EtOAc (15 ml), cooled to 0° C., saturated with HCl (g), and stirred 15 minutes. The solvent was removed in vacuo. The residue was treated with EtOAc and restripped (3x) to give a white solid (410 mg).
TLC (as free base): silica GF (80/10/1 of CH$_2$Cl$_2$/MeOH/concentrated NH$_4$OH), R$_f$=0.46, single homogeneous component.
The white solid (320 mg) was combined with Boc(DNP)His—OH (371 mg) and TEA (0.321 ml) in CH$_2$Cl$_2$ (15 ml) and treated with 1M DCC in CH$_2$Cl$_2$ (0.843 ml). The reaction was stirred 16 hours at 25° C., the solvent removed in vacuo, the residue treated with EtOAc, and the precipitate (DCU) removed by filtration. The filtrate was washed with 10% NaHCO$_3$ (aqueous) (1x) and brine (1x), dried over MgSO$_4$, filtered, and stripped to dryness in vacuo to give a yellow oil (800 mg). Flash chromatography of the crude oil on silica gel (200/10/1 of CH$_2$Cl$_2$/MeOH/concentrated NH$_4$OH) provided 8 as a yellow film (140 mg).
TLC: silica GF (80/10/1 of CH$_2$Cl$_2$/MeOH/concentrated NH$_4$OH), R$_f$=0.78, single homogeneous component.

N$^\alpha$-[4(S)-(tert-Butoxycarbonyl-L-phenylalanyl-2,4-dinitrophenyl-L-histidylamino)-3(S)-hydroxy-6-methylheptyl]-L-leucine benzylamide 9

8 (140 mg) was dissolved in EtOAc (5 ml), cooled to 0° C., saturated with HCl (g) and stirred 15 minutes. The solvent was removed in vacuo. The residue was treated with EtOAc and restripped (3x) to give a white solid (150 mg). TLC (as free base): silica GF (80/10/1 of CH$_2$Cl$_2$/MeOH/concentrated NH$_4$OH), R$_f$=0.53. The white solid (143 mg) was conbined with Boc-Phe-OH (61.5 mg), TEA (107 μl), NaHCO$_3$(solid) (124 mg) and sodium azide (15.7 mg) in DMF (5 ml) and cooled to −30° C. under a nitrogen atmosphere. The mixture was treated with DPPA (58 μl) and stirred 16 hours at 0° C. After removal of the DMF in vacuo, the residue was treated with H$_2$O and extracted with EtOAc (3x). The combined extracts were washed with 10% NaHCO$_3$ (aqueous) (1x) and brine (1x), dried over MgSO$_4$, filtered, and stripped to dryness in vacuo to give a crude yellow foam (210 mg). Flash chromatography on silica gel (300/10/1 of CH$_2$Cl$_2$/MeOH/concentrated NH$_4$OH) gave desired 9 (100 mg).

TLC: silica GF (300/10/1 of CH₂Cl₂/MeOH/concentrated NH₄OH), essentially clean component.
PMR: consistent with structure.
MS (FAB): m.w.=419 m/e (M+H).

N^α-[4(S)-tert-Butoxycarbonyl-L-phenylalanyl-L-histidylamino)-3(S)-hydroxy-6-methyl-1-heptyl]-L-leucine benzylamide 10

9 (100 mg) was treated with 10% thiophenol in DMF (2 ml) and the reaction stirred 15 minutes at 25° C. After removal of the DMF in vacuo, the residue was treated with 10% citric acid and extracted with EtOAc (3x). The combined extracts were washed with H₂O (1x), 10% NaHCO₃ (aqueous) (1x) and brine (1x), dried over MgSO₄, filtered, and stripped to dryness in vacuo to give a yellow foam (90 mg). Flash chromatography on silica gel (180/10/1/1 of CH₂Cl₂/MeOH/H₂O/HOAc) provided 10 as a light yellow foam (40 mg).

TLC: silica GF (80/10/1 of CH₂Cl₂/MeOH/concentrated NH₄OH), R_f=0.62, clean homogeneous component.
PMR: consistent with product.
HPLC: 97.6%.
MS (FAB): m.w.=748 m/e (M+H).
SPINCO: calc'd: His, 1.34; Phe, 1.34. Found: His, 1.24; Phe, 1.22.

What is claimed is:

1. A compound having the formula:

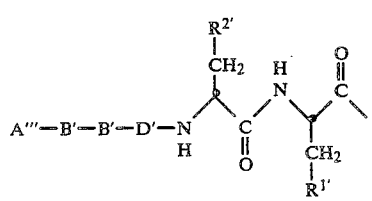

wherein:
A is
(i)

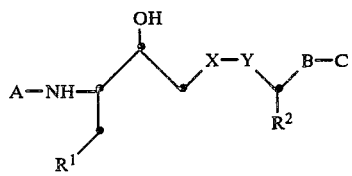

where:
A″ is hydrogen or phenoxyacetyl;
(ii)

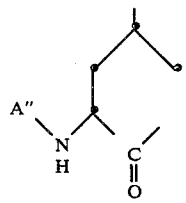

where:
A‴ is hydrogen;

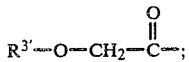

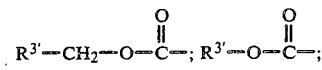

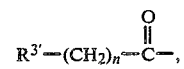

wherein n is 0-5; or

where R³′ has the same meaning as set out further below or hydrogen;
B′ is absent; glycyl; or

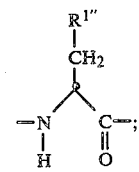

D′ is absent; or

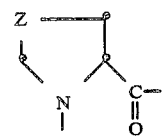

where Z is (CH₂)_n and n is 1 or 2; or —S—;
R¹′ or R¹″ is hydrogen; C₁₋₄alkyl; hydroxy C₁₋₄alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine C₂₋₄alkyl; guanidyl C₂₋₃alkyl; or methylthiomethyl;
R²′ is hydrogen; C₁₋₄alkyl; phenyl; phenyl mono-substituted with a member selected from the group consisting of methyl, trifluoromethyl, hydroxy, methoxy, fluoro, chloro, bromo, and iodo; or indolyl; and
R³′ is C₃₋₆alkyl; C₃₋₇cycloalkyl; phenyl; or phenyl mono-substituted with a member selected from the group consisting of methyl, trifluoromethyl, hydroxy, methoxy, fluoro, chloro, bromo, and iodo;
(iii)

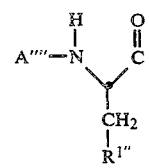

where:
A″″ is hydrogen; or

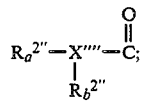

wherein:
X'''' is

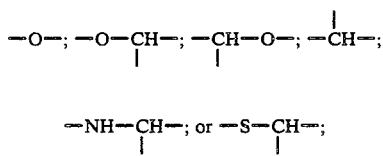

and
$R_a^{2''}$ and $R_b^{2''}$ are independently hydrogen; Y'—(CH$_2$)$_n$— or Y'—(CH$_2$)$_m$ —CH═CH—(CH$_2$)$_{p'}$ where Y' is hydrogen; aryl; aryl substituted with up to five members independently selected from the group consisting of C$_{1-8}$alkyl, trifluoromethyl, hydroxy, C$_{1-4}$alkoxy, and halo; n is 0 to 5; m is 0 to 2; and p is 0 to 2; except that where X'''' is —O—, only one of $R_a^{2''}$ or $R_b^{2''}$ is present; and $R^{1''}$ is hydrogen; C$_{1-4}$alkyl, provided, that where $R^1$ is i-propyl, and B is Phe or Tyr, A is other than hydrogen or phenoxyacetyl; hydroxy C$_{1-4}$alkyl; aryl; aryl substituted with up to three members selected from the group consisting of C$_{1-4}$alkyl, trifluoromethyl, hydroxy, C$_{1-4}$alkoxy; fluoro, chloro, bromo, and iodo; indolyl; 4-imidazolyl; amine C$_{2-4}$alkyl; guanidyl C$_{2-3}$alkyl; or methylthiomethyl;

X—Y is

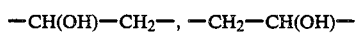

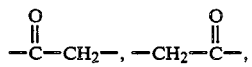

trans-CH═CH—

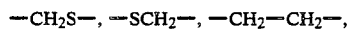

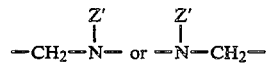

wherein
Z' is H, CH$_3$, (CH$_2$)$_n$B'', (CH$_2$)$_n$C''
wherein
n is 0–4, or

wherein
$R_a$ is C$_1$-C$_6$alkyl, ar-C$_{1-6}$-alkyl, C$_{3-7}$cycloalkyl; C$_{1-6}$alkoxy; aryl or heteroaryl;

$R^1$ is C$_1$-C$_4$ branched or linear alkyl, C$_3$-C$_6$cycloalkyl, phenyl or monosubstituted phenyl where the substituent is OH, Cl, Br, F, CH$_3$, CF$_3$, I or OCH$_3$;

$R^2$ is hydrogen or

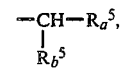

wherein
$R_a^5$ and $R_b^5$ are independently selected from hydrogen, C$_1$-C$_4$alkyl, hydroxy or C$_3$-C$_7$cycloalkyl;

B'' is

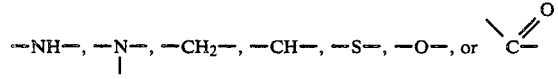

C'' is NH$_2$, NHCH$_2$R$^{3''}$, —NH— or

wherein
$R^{3''}$ is C$_3$-C$_6$alkyl, C$_3$-C$_7$ cycloalkyl, phenyl or monosubstituted phenyl wherein the substituent is methyl, trifluoromethyl, hydroxy, methoxy, fluoro, chloro, bromo or iodo; and B—C is

wherein $R^6$ is selected from:
(a) OR; NHR; or NR$_2$, where each R is independently hydrogen or C$_{1-4}$alkyl;
(b) B''''—E wherein
  B'''' is absent; glycyl;

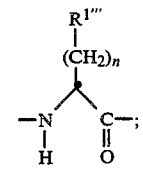

wherein
n is 1 or 2; or —S—;
$R^{1'''}$ is hydrogen; C$_{1-4}$alkyl; hydroxy C$_{1-4}$alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine C$_{2-4}$alkyl; guanidyl C$_{2-3}$alkyl; or methylthiomethyl; and
E is OR; NHR, or N(R)$_2$, where each R is independently hydrogen or C$_{1-4}$alkyl; and
(c) B°—D—E wherein
  B° is —Y—(CH$_2$)$_n$—R$^{6a}$ (1)
where
Y is —NH— or —O—;
n is 0 to 5; and
$R^{6a}$ is hydrogen, hydroxy; C$_{1-4}$alkyl; C$_{3-7}$cycloalkyl; aryl; aryl substituted with up to five members independently selected from the group consisting of C$_{1-6}$alkyl, trifluoromethyl, hydroxy, C$_{1-4}$alkoxy, amino, mono- or di-C$_{1-4}$alkylamino, and halo; amino;

mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

(2) 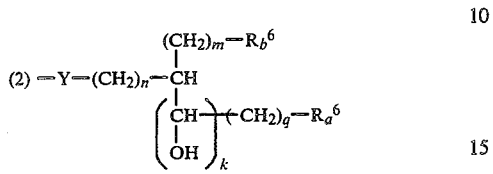

where
Y is as defined above;
n is 0 or 1;
k is 0 or 1;
q is 1 to 4;
m is 1 to 4. and
$R_b^6$ and $R_a^6$ are each independently the same as $R^{6a}$ above and $R_a^6$ may additionally be

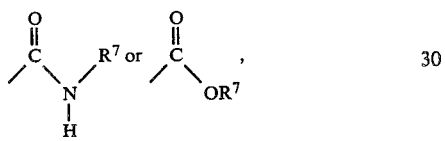

where $R^7$ is hydrogen or $C_{1-3}$alkyl;

(3) 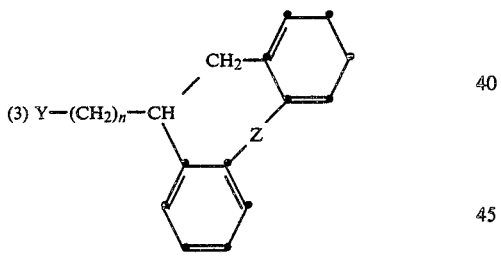

where
Y is as defined above;
n is 0 or 1; and
Z is (a) 

where
n is 0 or 1; and
$R^7$ is as defined above; or (b) 

where
n is 0 or 1; or (4) 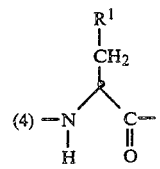

where $R^1$ is as defined above;
D is absent; glycyl; sarcosyl; or

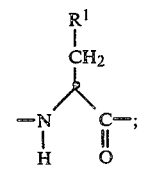

and
E is absent; OR; NHR; or $N(R)_{2'}$ where R is independently hydrogen or $C_{1-4}$alkyl;

(d) —Y—$(CH_2)_n$—$R_a^6$
where
Y is —NH— or —O—;
n is 0 to 5; and
$R_a^6$ is hydrogen;

$C_{1-3}$alkyl; $C_{3-7}$cycloalkyl; naphthyl; phenyl; phenyl substituted with up to five members independently selected from the group consisting of methyl, trifluoromethyl, hydroxyl, methoxy, amino, fluoro, chloro, bromo, and iodo; imidazolyl; pyridyl; pyrryl; hydroxyl; amino; $C_{1-4}$alkyl mono-, di-, or tri-substituted amino; guanidyl; piperidyl; tetrahydropyrryl; or N-substituted piperidyl or tetrahydropyrryl where the N-substituent is a member selected from the group consisting of hydrogen, $C_{1-6}$alkyl, $C_{1-6}$hydroxyalkyl, phenyl, benzyl, naphthyl, and naphthylmethyl;

(e)

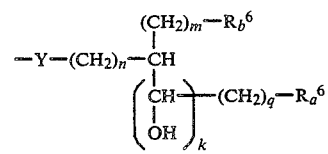

where
Y is as defined above;
n is 0 or 1;
k is 0 or 1;
q is 1 to 4;
m is 1 to 4; and
$R_b^6$ and $R_a^6$ are each independently the same as $R^{6a}$ above; or (f)

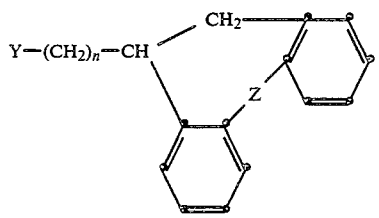
where
Y is as defined above;
n is 0 or 1; and
Z is
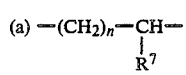
where
n is 0 or 1; and
R⁷ is hydrogen or
$C_{1-3}$alkyl; or
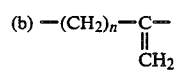
where
n is 0 or 1;
and pharmaceutically acceptable salts thereof.
2. A compound of claim 1 that is
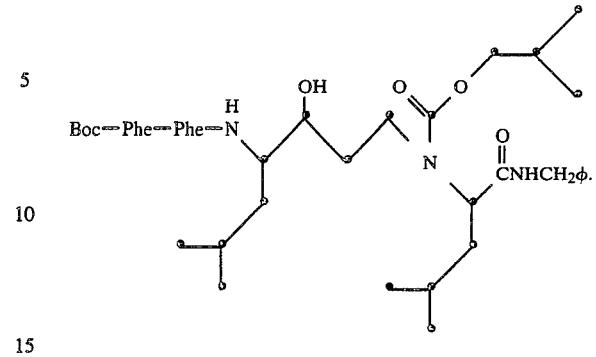
3. A compound of claim 1 that is
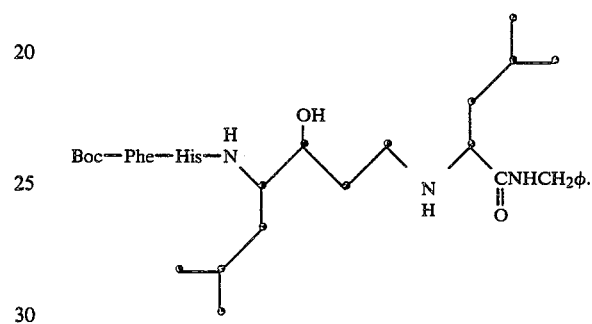
4. A pharmaceutical composition for treating hypertension or hyperaldosteronism containing an effective amount of a compound of claim 1 and a carrier.
* * * * *